United States Patent
Peesapati et al.

(10) Patent No.: US 11,160,503 B2
(45) Date of Patent: Nov. 2, 2021

(54) WEARABLE CONTINUOUS VASCULAR ACCESS MONITOR

(71) Applicant: Fresenius Medical Care Holdings, Inc., Waltham, MA (US)

(72) Inventors: Sameera Anirudh Peesapati, Pittsburg, CA (US); Joseph Edwin Inase Manakkil, San Ramon, CA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 90 days.

(21) Appl. No.: 16/391,822

(22) Filed: Apr. 23, 2019

(65) Prior Publication Data

US 2020/0337638 A1   Oct. 29, 2020

(51) Int. Cl.
*A61B 5/00* (2006.01)
*A61B 5/02* (2006.01)
(Continued)

(52) U.S. Cl.
CPC .......... *A61B 5/6824* (2013.01); *A61B 5/0022* (2013.01); *A61B 5/02042* (2013.01);
(Continued)

(58) Field of Classification Search
CPC . A61B 5/6824; A61B 5/0022; A61B 5/02042; A61B 5/150992; A61B 5/6802; A61B 5/746; A61B 5/02007; A61B 5/02055; A61B 5/742; A61B 2560/0204; A61B 2560/0462; A61M 1/3655;
(Continued)

(56) References Cited

U.S. PATENT DOCUMENTS

| | | | | | |
|---|---|---|---|---|---|
| 6,153,109 A | * | 11/2000 | Krivitski | ............. | A61M 1/3653 210/646 |
| 2001/0007930 A1 | * | 7/2001 | Kleinekofort | ....... | A61M 1/3621 604/4.01 |

(Continued)

OTHER PUBLICATIONS

Chiang et al. "A Novel Wireless Photoplethysmography Blood-Flow Volume Sensor for Assessing Arteriovenous Fistula of Hemodialysis Patients," *IEEE Transactions on Industrial Electronics*, 64 (12) (Dec. 2017).

(Continued)

*Primary Examiner* — Carl H Layno
*Assistant Examiner* — Manolis Pahakis
(74) *Attorney, Agent, or Firm* — Leydig, Voit & Mayer, Ltd.

(57) ABSTRACT

A system for monitoring a vascular access is provided. The system includes a wearable vascular access monitor which can be a sleeve or other protective covering fitted with two or more sensors for obtaining physiological measurements at different locations from the vascular access. The sleeve or other protective covering is also fitted with an ultra-low power processor for relaying the physiological measurements to a patient's mobile phone. The patient's phone can evaluate the physiological measurements to determine a state of the vascular access, and if the physiological measurements fall out of nominal ranges, the patient's phone can alert a clinic, nurse, or physician. The system can be used to monitor fistulas or grafts used for hemodialysis or peritoneal dialysis.

26 Claims, 7 Drawing Sheets

(51) Int. Cl.
  *A61B 5/15* (2006.01)
  *A61M 1/36* (2006.01)
  *A61B 5/0205* (2006.01)
  *A61M 1/16* (2006.01)

(52) U.S. Cl.
  CPC ...... *A61B 5/150992* (2013.01); *A61B 5/6802* (2013.01); *A61B 5/746* (2013.01); *A61M 1/3655* (2013.01); *A61B 5/02007* (2013.01); *A61B 5/02055* (2013.01); *A61B 5/742* (2013.01); *A61B 2560/0204* (2013.01); *A61B 2560/0462* (2013.01); *A61B 2562/0204* (2013.01); *A61B 2562/0219* (2013.01); *A61B 2562/0271* (2013.01); *A61M 1/1601* (2014.02); *A61M 1/3656* (2014.02); *A61M 2205/3334* (2013.01); *A61M 2205/3375* (2013.01)

(58) Field of Classification Search
  CPC .............. A61M 1/1601; A61M 1/3656; A61M 2205/3334; A61M 2205/3375
  See application file for complete search history.

(56) References Cited

U.S. PATENT DOCUMENTS

| | | | | |
|---|---|---|---|---|
| 2002/0045836 | A1* | 4/2002 | Alkawwas | A61B 5/0006 600/509 |
| 2008/0195060 | A1* | 8/2008 | Roger | A61M 1/3653 604/246 |
| 2009/0120864 | A1 | 5/2009 | Fulkerson et al. | |
| 2009/0131767 | A1* | 5/2009 | Arne | A61M 1/3655 600/302 |
| 2009/0234261 | A1* | 9/2009 | Singh | A61B 17/1325 601/152 |
| 2010/0274172 | A1* | 10/2010 | Guenther | A61M 1/3646 604/6.11 |
| 2012/0273354 | A1* | 11/2012 | Orhan | A61M 1/28 204/519 |
| 2012/0273415 | A1* | 11/2012 | Gerber | A61B 5/0537 210/636 |
| 2013/0025697 | A1* | 1/2013 | Blasek | A61M 1/3652 137/15.05 |
| 2013/0299399 | A1* | 11/2013 | Suffritti | B01D 61/32 210/137 |
| 2014/0088483 | A1* | 3/2014 | Fontanazzi | A61M 1/1605 604/6.09 |
| 2014/0207062 | A1* | 7/2014 | Eagle | A61B 5/02152 604/111 |
| 2014/0350513 | A1* | 11/2014 | Oruklu | A61M 5/16854 604/505 |
| 2014/0358077 | A1* | 12/2014 | Oruklu | A61M 5/365 604/111 |
| 2015/0343129 | A1* | 12/2015 | Surace | A61M 1/3607 604/6.09 |
| 2016/0377530 | A1 | 12/2016 | Barrett | |
| 2017/0027499 | A1 | 2/2017 | Shuler | |
| 2017/0165007 | A1* | 6/2017 | Laufer | A61M 25/10 |
| 2017/0231565 | A1 | 8/2017 | Olivarez | |
| 2017/0325749 | A1* | 11/2017 | Shah | A61B 5/14546 |
| 2017/0340801 | A1* | 11/2017 | Roger | A61N 1/00 |
| 2018/0070841 | A1 | 3/2018 | Honore et al. | |
| 2018/0085261 | A1* | 3/2018 | Pan | A61F 13/10 |
| 2018/0126062 | A1* | 5/2018 | Solem | A61M 1/3656 |
| 2018/0318486 | A1* | 11/2018 | Crnkovich | A61M 1/3612 |
| 2020/0000355 | A1* | 1/2020 | Khair | A61N 1/36103 |
| 2020/0324038 | A1* | 10/2020 | Bloomberg | A61M 1/1601 |
| 2020/0330011 | A1* | 10/2020 | Honore | A61B 5/14552 |
| 2020/0337638 | A1* | 10/2020 | Peesapati | A61B 5/0022 |

OTHER PUBLICATIONS

Lin el al. "Assistive Technology Using Integrated Flexible Sensor and Virtual Alarm Unit for Blood Leakage Detection During Dialysis Therapy", *Healthcare Technology Letters* (Dec. 2016).

Panda et al. "Flexible, Skin Coupled Microphone Array for Point of Care Vascular Access Monitoring," *IEEE Trans Biomed Circuits Syst*. (Dec. 2019).

International Patent Application No. PCT/US2020/028085, International Search Report (dated Jul. 7, 2020).

* cited by examiner

WEARABLE CONTINUOUS VASCULAR ACCESS MONITOR

BACKGROUND

Patients with kidney failure or partial kidney failure typically undergo hemodialysis treatment, often at a hemodialysis treatment center or clinic. When healthy, kidneys maintain the body's internal equilibrium of water and minerals (e.g., sodium, potassium, chloride, calcium, phosphorous, magnesium, and sulfate). In hemodialysis, blood is taken from a patient through an intake needle (or catheter) which draws blood from an artery located in a specific accepted access location (arm, thigh, subclavian, etc.). The drawn blood is pumped through extracorporeal tubing via a peristaltic pump, and then through a special filter called a dialyzer. The dialyzer is intended to remove unwanted toxins such as blood urea, nitrogen, potassium, and excess water from the blood. The dialyzed blood then flows out of the dialyzer via tubing and a needle (or catheter) back into the patient.

Vascular access is used for hemodialysis. These accesses are expected to sustain blood flow rates above 300 mL/min. One type of access is the arteriovenous fistula (AVF). AVF is considered to be the most effective of the vascular accesses for dialysis patients. One reason AVFs are effective is that they use native blood vessels, which, compared to synthetic grafts, are less likely to develop stenosis and fail. AVFs for hemodialysis typically include a surgically created connection between an artery and a vein in the arm. Artery walls are thicker than vein walls, and since the AVF connects the artery and the vein, the walls of the veins become thicker due to higher arterial pressure. The strengthened vein can then tolerate needles during hemodialysis.

SUMMARY

In an exemplary embodiment, a system for monitoring a vascular access includes a wearable vascular access monitor and a client device. The wearable vascular access monitor includes: a plurality of sensors placed at different locations in relation to the vascular access, the plurality of sensors configured to provide physiological measurements corresponding to the different locations; and a communication interface configured to facilitate communications with a client device. The client device is configured to: determine, using the physiological measurements, differential readings between pairs of sensors in the plurality of sensors, determine whether the differential readings exceed a first threshold, and send an alert to an emergency device in response to the differential readings exceeding the first threshold.

In another exemplary embodiment, one or more non-transitory computer-readable media have processor-executable instructions stored thereon for monitoring a vascular access. The processor-executable instructions, when executed, facilitate: receiving, from a plurality of sensors of a wearable access monitor placed at different locations in relation to the vascular access, physiological measurements corresponding to the different locations; determining differential readings between pairs of sensors in the plurality of sensors using the physiological measurements; determining whether the differential readings exceed a first threshold; and sending an alert to an emergency device in response to the differential readings exceeding the first threshold.

In yet another exemplary embodiment, a wearable vascular access monitor for monitoring a vascular access includes a plurality of sensors and a communication interface. The plurality of sensors placed at different locations in relation to the vascular access and are configured to provide physiological measurements corresponding to the different locations. The communication interface is configured to facilitate communications with another device.

In yet another exemplary embodiment, a dialysis system comprises a dialysis machine, a wearable vascular access monitor, and a gateway. The dialysis machine is configured to interface with a vascular access and filter blood obtained via the vascular access. The wearable vascular access monitor includes: a plurality of sensors placed at different locations in relation to the vascular access, the plurality of sensors configured to provide physiological measurements corresponding to the different locations. The gateway is configured to facilitate communications between the dialysis machine and an external network and between the wearable vascular access monitor and the external network.

DETAILED DESCRIPTION

Although AVFs are effective accesses for patients undergoing hemodialysis, there are constraints that lead AVFs to fail. AVFs can become infected because they are exposed sites that facilitate removing blood from patients and reintroducing blood to the patients. Patients undergo hemodialysis about three times a week so there are multiple opportunities during the week for the AVF to become infected. Furthermore, AVFs can fail due to stenosis, improper maintenance during maturation period, hematoma, and a patient's overall lack of awareness.

The United States government has mandated that health providers increase prevalence of AVF; as such, AVF has been made a part of the quality guidelines for clinics. The increased use of AVF has led to identifying the following issues: (1) creating more patient awareness and confidence that maintenance of AVF is easy; (2) cost of fixing a failed fistula; (3) ensuring patient visits for regular checks; (4)

availability of vascular surgeons; (5) techniques for monitoring an AVF used by clinicians are empirical; (6) time between measurements is on average four weeks for patients once they start dialysis with current technologies available in dialysis access care centers. Current AVF monitoring technologies are invasive and are usually performed once every four weeks. In these technologies, blood is recirculated, and an ultrasound or ultrasonic sensor is used to monitor the blood recirculation to determine whether the AVF is performing well.

Embodiments of the disclosure provide a wearable continuous fistula monitor designed to utilize different sensors to detect onset of infection growth, clots from stenosis, and changes in the local area occurring due to improper maintenance. Embodiments of the disclosure provide subjective assessments for whether an AVF is fine or whether an AVF is at risk. Embodiments of the disclosure alert a clinic or an emergency contact to intervene when the AVF is at risk. As such, the intervention can come at a timely fashion to prevent further damage to the AVF. The patient's AVF is thus monitored more frequently, even continuously, as opposed to every four weeks in conventional methods.

Figure 1A:
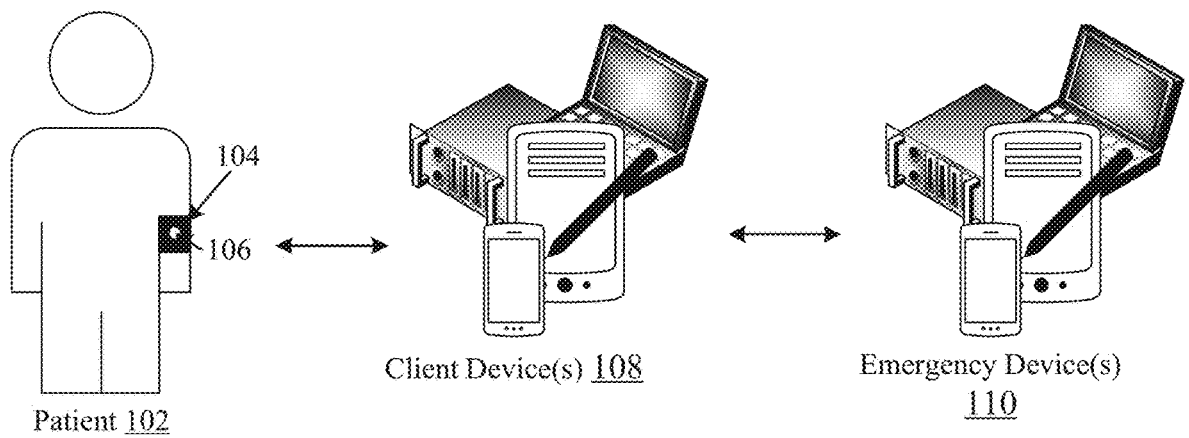
FIG. 1A illustrates an example environment for monitoring a vascular access according to some embodiments of the disclosure.

FIG. 1A illustrates an example environment for monitoring a vascular access according to some embodiments of the disclosure. A patient 102 with a vascular access or access point 106 wears a wearable vascular access monitor 104. The patient 102 may be a dialysis patient, and the access point 106 may be an AVF. The wearable vascular access monitor 104 may be a sleeve or other protective covering that the patient 102 slips on or secures on his arm. The wearable vascular access monitor 104 can be used to monitor vascular accesses on other parts of the body. FIG. 1A illustrates an example of monitoring the access point 106 on the arm of the patient 102.

The patient 102 pairs the wearable vascular access monitor 104 with one or more client devices 108. The one or more client devices 108 receives monitoring data from the wearable vascular access monitor 104 and provides calibration settings to the wearable vascular access monitor 104. Examples of the one or more client devices 108 include smartphones, laptop computers, desktop computers, computer servers, smart watches, tablets, and so on. The one or more client devices 108 can perform analysis on the monitoring data received and based on determining that the access point 106 is at risk, can alert one or more emergency devices 110. The one or more emergency devices 110 may be a smartphone, laptop computer, desktop computer, computer server, smart watch, tablet, beeper, and so on.

Figure 1B:
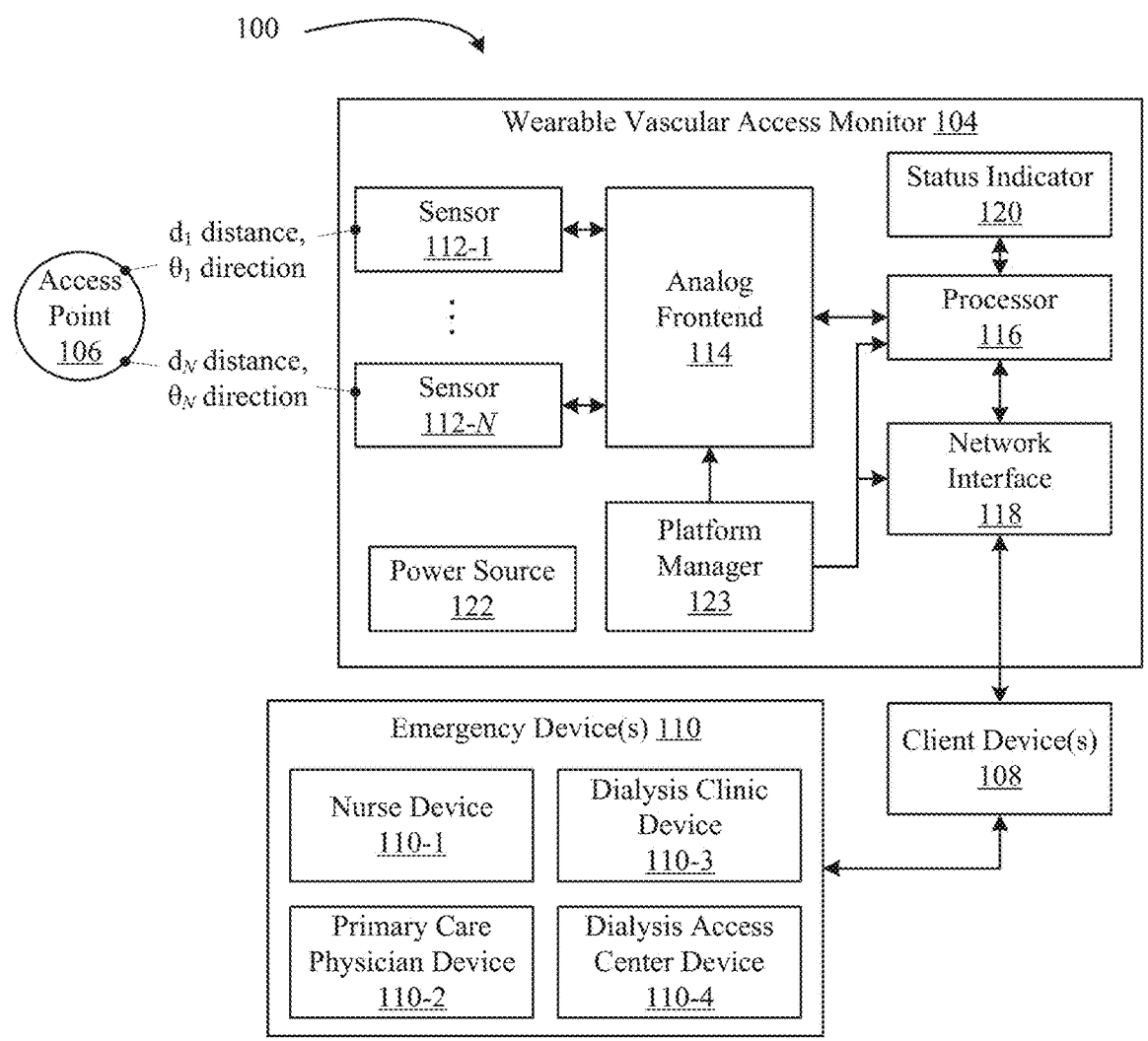
FIG. 1B illustrates an example system for monitoring a vascular access according to some embodiments of the disclosure.

FIG. 1B illustrates an example system 100 for monitoring a vascular access according to some embodiments of the disclosure. FIG. 1B further illustrates components of the wearable vascular access monitor 104 and various types of emergency devices 110. In FIG. 1B, the wearable vascular access monitor 104 includes two or more sensors 112-1 to 112-N. Using the center of the access point 106 for orientation, each sensor 112-$x$ is located a distance $d_x$ from the access point 106 at a direction $\theta_x$. Examples of sensors 112-1 to 112-N include pressure sensors, temperature sensors, oxygen saturation SpO2 sensors, color sensors (RGB color or XYZ spectral sensors), ultrasonic time-of-flight sensors, force sensors like accelerometers, and so on. The sensors 112-1 to 112-N generate sensor data by measuring conditions at specific locations relative to the location of the access point 106.

The wearable vascular access monitor 104 includes an analog frontend 114 for conditioning and processing the sensor data generated. Signal conditioning can include preparing signal levels of sensor data of each of sensors 112-1 to 112-N so that analogous data can be compared. Signal processing of the sensor data can include using tunable hardware filters to remove artifacts within the sensor data. The analog frontend 114 can further include an analog to digital converter for providing the sensor data as digital representation to a processor 116.

The wearable vascular access monitor 104 includes the processor 116 which performs further preparation of the sensor data for transmission. The processor 116 can be an ultra-low power processor, a field programmable gate array (FPGA), a complex programmable logic device (CPLD), and so on.

The wearable vascular access monitor 104 includes a network interface 118. The network interface 118 allows communication with the client device(s) 108. The wearable vascular access monitor 104 can send status and monitoring data prepared by the processor 116 to the client device(s) 108. The wearable vascular access monitor 104 can also receive settings and calibration from the client device(s) 108. The wearable vascular access monitor 104 may support communication via multiple types of networks. The network interfaces 118 may include optical transceivers or radio frequency transceivers. Examples of network interfaces 118 include radios compatible with several Wi-Fi standards, 3G, 4G, Long-Term Evolution (LTE), Bluetooth®, Zigbee, and so on.

The wearable vascular access monitor 104 includes a status indicator 120. The status indicator 120 can include one or more light emitting diode (LED) lights for providing visual indications. The LED lights can indicate that the wearable vascular access monitor 104 is functioning/not functioning properly and/or the access point 106 is/is not at risk. In some embodiments, since functioning properly is expected most of the time, the LED lights only turn on to indicate that something is wrong; this way, the LED lights do not consume energy during normal operation. The status indicator 120 can also include one or more auditory indicators like a speaker that beeps when the wearable vascular access monitor 104 is either not functioning properly or when the access point 106 is at risk. In some embodiments, the status indicator 120 provides a visual and/or auditory indication when the wearable vascular access monitor 104 first comes online.

The wearable vascular access monitor 104 includes a power source 122 for providing power to the different components described. In some embodiments, the power source 122 is a battery or a rechargeable battery.

The wearable vascular access monitor 104 includes a platform manager 123. The platform manager 123 is programmable hardware, e.g., an FPGA or a CPLD that serves three functions. The platform manager 123 performs platform management, power management, and security enforcement. For platform management, the platform manager 123 manages board level critical tasks for the wearable vascular access monitor 104. Platform management can include ensuring sensor data integrity and operational stability control. For example, the platform manager 123 receives data from the sensor 112-1. The data from the sensor 112-1 is appended with an authentication code where the platform manager 123 checks this authentication code against a code from the sensor 112-1 to determine whether the data came from the specific sensor.

Platform management can also include monitoring safety critical status signals and critical signal integrity. Safety critical status signals are signals assigned to represent safe operating limits of the wearable vascular access monitor 104. An example includes power monitoring signals that define status of the power source 122. The power monitoring signals can indicate a remaining power level where the platform manager 123 determines whether the remaining power level is adequate to provide trustable information from the sensors 112. For example, if remaining power level falls below a predefined level, then the platform manager 123 enforces safety protocols. The safety protocols include operational safety protocols and/or human safety protocols. An operational safety protocol can involve storing present data, setting a warning indicator (e.g., blinking orange light from a tri-color LED of the status indicator 120), reducing sampling rate for the sensors 112, and reducing signal processing rate at the analog frontend 114 and/or the processor 116.

In some embodiments, human operational control include sounding an alarm via speakers in the status indicator 120 to check for a short circuit that can create high current and may cause burning.

In some embodiments, signals integrity of safety critical status signals cannot be trusted to enforce correct safety protocols. The platform manager 123 determines whether the signal has too much noise susceptibility. Signals with too much noise susceptibility include, for example, unstable signals due to poor circuit design, unstable signals due to susceptibility to changes in ambient temperature, and unstable signals due to electromagnetic compatibility (EMC) compliances. The platform manager 123 also checks for unintended reset and abnormal loading of configuration and calibration data.

Platform management can also include emergency control enforcing for safety critical parameters and functionality. Platform management can also include sensor calibration status check with respect to stored baseline data. Platform management can also include control and retention of factory calibration data, sensor functional/operational configuration data, and/or the wearable vascular access monitor 104 functional/operational configuration data. Platform management can further include system alarm and safe operating limits management. Platform management can also include safeguarding boot code of the platform manager 123 from corruption from one or more forms of unauthorized/undesired changes.

Power management of the platform manager 123 involves power sequencing and reset processing, power monitoring, power management and optimizations for longer time-between-recharge and for performance optimizations, and power emergency controls. Power emergency controls include safety protocol management and safe management of sensor data when available operating power is below a safe operating threshold, as discussed above.

Security enforcement of the platform manager 123 includes cybersecurity guard/compliance enforcement for secure and safe operation of hardware and software of the wearable vascular access monitor 104. Security enforcement includes security key management for master authentication and encryption and decryption engines for secure signal and/or data processing, transfer, and storage. In master authentication, a security key is transferred from a manufacturing site of the wearable vascular access monitor 104 (after factory acceptance tests) to authenticate and enable secure engine functionality. At the manufacturing site, device operational configuration files can be loaded, calibrated, and tested before approval for customer delivery. Security enforcement also includes threat monitoring and critical event logging, e.g., logging of safety and security events, logging of remote accesses to the wearable vascular access monitor 104, and so on. Security enforcement can also include a safety and security mode (including internal and external data management and communication/data transfer).

The client device(s) 108 can contact emergency device(s) 110 whenever the access point 106 is determined to be at risk. Emergency device(s) 110 can include a nurse device 110-1 which can be, e.g., a smartphone of a nurse responsible for the patient 102. Emergency device(s) 110 can include a primary care physician (PCP) device 110-2 which can be, e.g., a smartphone of the PCP of the patient 102. Emergency device(s) 110 can include a dialysis clinic device 110-3 or a dialysis access center device 110-4, which can be, e.g., a telephone, smartphone, computer, and so on.

It will be appreciated that the embodiments depicted in FIGS. 1A and 1B are merely exemplary, and that other exemplary implementations are usable. For example, in another exemplary embodiment, the functions performed by the client device(s) 108 may be performed by one or more processors of the wearable vascular access monitor itself 104, such that the wearable vascular access monitor 104 can perform analysis on the monitoring data received from the sensors and based on determining that the access point 106 is at risk, can alert one or more emergency devices 110.

Figure 2:
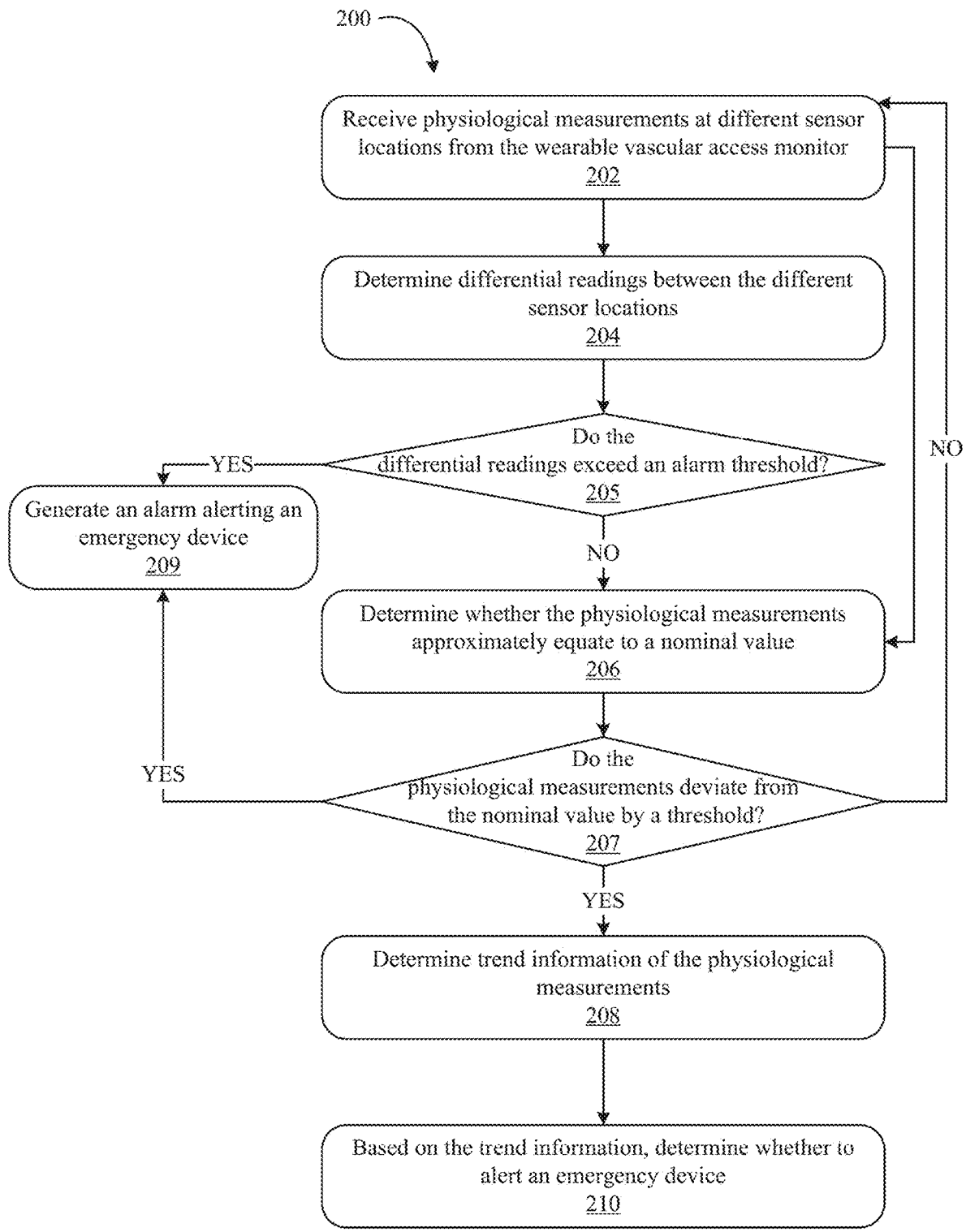
FIG. 2 is a flow diagram illustrating a process for alerting one or more emergency devices of a status of a vascular access according to some embodiments of the disclosure.

FIG. 2 is a flow diagram illustrating a process 200 for alerting one or more emergency devices of a status of a vascular access according to some embodiments of the disclosure. At 202, the client device 108 receives physiological measurements at different sensor locations from the wearable vascular access monitor 104.

At 204, the client device 108 determines differential readings between the different sensor locations based on the physiological measurements. The client device 108 incorporates mutual distances between the sensor locations and distances between the access point 106 and the sensor locations with the physiological measurements to determine the differential readings between the different sensor locations.

At 205, in an embodiment, the client device 108 determines whether the differential readings exceed an alarm threshold. And if an alarm threshold is exceeded, then at 209, the client device 108 generates an alarm alerting an emergency device that differential readings between measurements taken at two or more sensor locations exceed the alarm threshold.

At 206, the client device 108 determines whether the physiological measurements approximate a nominal value. In an embodiment, the physiological measurements approximate the nominal value when the physiological measurements are within 1% of the nominal value. A state where the physiological measurements approximate the nominal value can be called an equilibrium state.

At 207, the client device 108 determines whether the physiological measurements deviate from the nominal value by a threshold. In some embodiments, if the client device 108 determines that the physiological measurements deviate from the nominal value by a threshold, then at 209, the client device 108 generates an alarm alerting the emergency device.

In some embodiments, at 208, if the physiological measurements deviate from the nominal value by the threshold, the client device 108 determines trend information of the physiological measurements. Trend information includes watching the physiological measurements for a specified time period to determine whether the physiological measurements are steady, are rising, or are falling. A state where trend information is determined can be called a caution state.

At 210, the client device 108 determines whether to alert the emergency device based on the trend information.

As illustrated in FIG. 2, in some embodiments, the client device 108 can receive physiological measurements at 202 and then proceed to 206 to determine whether the physiological measurements approximately equate the nominal value.

Figure 3:
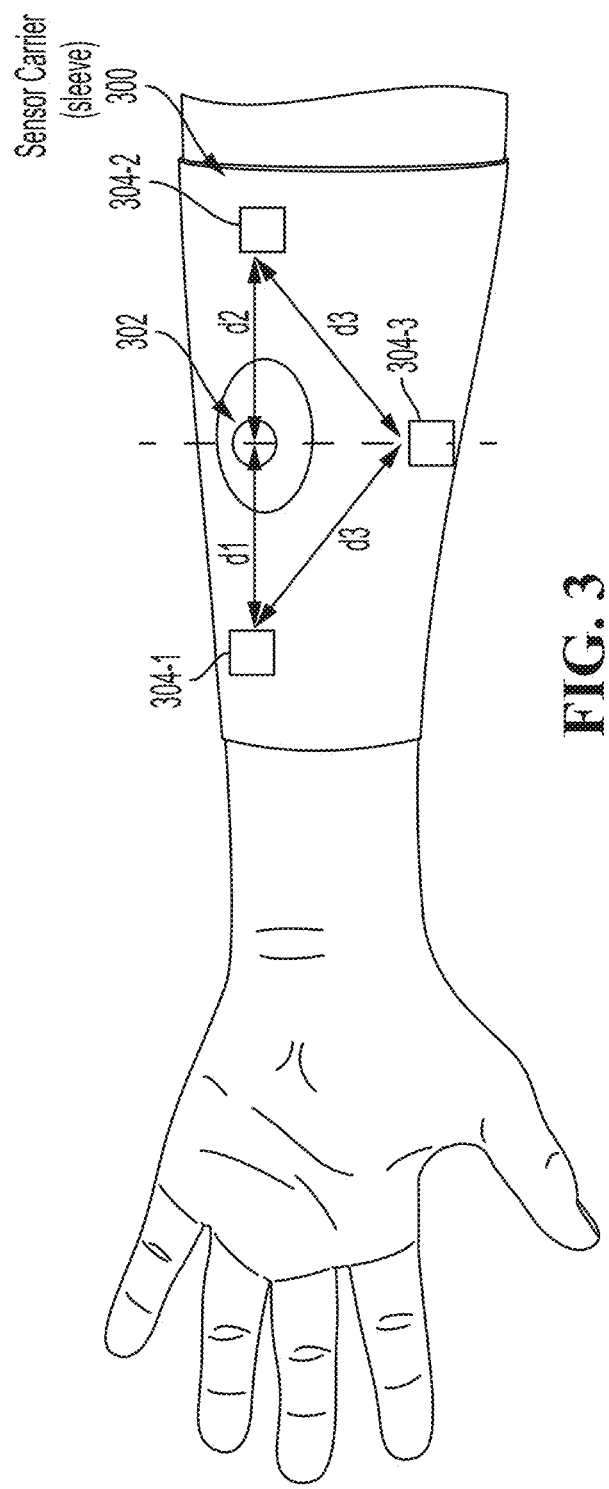
FIG. 3 illustrates a wearable vascular access monitor for differential temperature measurements according to some embodiments of the disclosure.

FIG. 3 illustrates a wearable vascular access monitor 300 for differential temperature measurements according to some embodiments of the disclosure. The wearable vascular access monitor 300 includes three temperature sensors 304-1, 304-2, and 304-3 placed at different locations from an access point 302. In an embodiment, the temperature sensors 304-1 and 304-2 are placed at opposite directions from the access point 302. The access point 302 is located on one side of the arm, and the temperature sensor 304-3 is located on the opposite side of the arm. The temperature sensor 304-3 location is chosen to be as far away from the access point 302 but equidistant to sensors 304-1 and 304-2.

The spatial distance from the access point 302 to the temperature sensor 304-1 is $d_1$. The spatial distance from the access point 302 to the temperature sensor 304-2 is $d_2$. The spatial distance from the temperature sensor 304-1 to the temperature sensor 304-3 is $d_3$, and the spatial distance from the temperature sensor 304-2 to the temperature sensor 304-3 is also $d_3$.

In an embodiment, having three readings from three different locations provides an area equivalent calculation for determining qualities of the access point 302. The different readings at the different locations when combined allow for performing trend analysis, developing standard deviations, and developing temperature data profiles and tracking algorithms. The multiple sensor configuration can provide deterministic and highly-reliable system decisions based on triple-redundant sensor data from two or more sensors. This allows decision based voting where a majority of sensors agreeing can be used as a strong bias towards determining whether a minority of sensors are faulty.

In an embodiment, the temperature sensors 304-1, 304-2, and 304-3 sample body temperature, in degrees Celsius, at their respective locations once every minute. The wearable vascular access monitor 300, thus collects sensor data every minute and packages and sends the sensor data after a prescribed amount of time to a client device (not shown) at step 202.

At step 204, using the spatial distances $d_1$, $d_2$, and $d_3$, and the temperature measurements in the sensor data of step 202, the client device can then determine differential temperature readings between the different sensors as provided in Eqs. 1-3. $d_1$ and $d_2$ can be 3-5 cm from the access point 302.

$$\int_{t.start}^{t.stop} \frac{d(T_1 d_1)}{dt} - \int_{t.start}^{t.stop} \frac{d(T_2 d_2)}{dt} \qquad \text{Eq. 1}$$

$$\int_{t.start}^{t.stop} \frac{d(T_1 d_1)}{dt} - \int_{t.start}^{t.stop} \frac{d(T_3 d_3)}{dt} \qquad \text{Eq. 2}$$

$$\int_{t.start}^{t.stop} \frac{d(T_2 d_2)}{dt} - \int_{t.start}^{t.stop} \frac{d(T_3 d_3)}{dt} \qquad \text{Eq. 3}$$

Eq. 1 is the differential temperature reading between the temperature sensors 304-1 and 304-2, where $T_1$ and $T_2$ are temperature measurements from the temperature sensors 304-1 and 304-2, respectively. Eq. 2 is the differential temperature reading between the temperature sensors 304-1 and 304-3, where $T_3$ is the temperature measurements from the temperature sensor 304-3. Eq. 3 is the differential temperature reading between the temperature sensors 304-2 and 304-3. $T_1$, $T_2$ and $T_3$ are temperature measurements over a time period (t.stop−t.start). Thus, Eqs. 1-3 find the difference between average temperature readings of the temperature sensors 304-1 and 304-2, the temperature sensors 304-1 and 304-3, and the temperature sensors 304-2 and 304-3, respectively.

From the temperature measurements $T_1$, $T_2$ and $T_3$ and the differential temperature readings of Eqs. 1-3, at 206, the client device determines whether each temperature measurement approximates a nominal temperature $T_{nom}$. In an embodiment, temperature measurements $T_1$, $T_2$ and $T_3$ should be within 1% of the nominal temperature $T_{nom}$. When $T_1$, $T_2$ and $T_3$ are within 1% of $T_{nom}$, the wearable vascular access monitor 300 maintains an equilibrium state. When any of $T_1$, $T_2$ or $T_3$ is not within 1% of $T_{nom}$, the wearable vascular access monitor 300 transitions to a caution state. The caution state signifies that the body temperature is either too high or too low.

In some embodiments, at 205, the differential temperature readings of Eqs. 1-3 can be used to determine whether to generate an alarm. In an embodiment, when Eq. 1, 2 or 3 is nonzero and the magnitude of Eq. 1, 2 or 3 evaluated exceeds an alarm threshold $T_{alarm}$, then an alarm is generated at 209. Eq. 4 summarizes this condition.

When $\left( \int_{t.start}^{t.stop} \frac{d(T_1 d_1)}{dt} > \right.$ Eq. 4

$\left. \int_{t.start}^{t.stop} \frac{d(T_2 d_2)}{dt} \text{ or } \int_{t.start}^{t.stop} \frac{d(T_1 d_1)}{dt} < \int_{t.start}^{t.stop} \frac{d(T_2 d_2)}{dt} \right)$ and $\left| \left( \int_{t.start}^{t.stop} \frac{d(T_1 d_1)}{dt} - \int_{t.start}^{t.stop} \frac{d(T_2 d_2)}{dt} \right) \right| > T_{alarm}$

OR

When $\left( \int_{t.start}^{t.stop} \frac{d(T_1 d_1)}{dt} > \int_{t.start}^{t.stop} \frac{d(T_3 d_3)}{dt} \right.$ $\left. \text{or } \int_{t.start}^{t.stop} \frac{d(T_1 d_1)}{dt} < \int_{t.start}^{t.stop} \frac{d(T_3 d_3)}{dt} \right)$ and $\left| \left( \int_{t.start}^{t.stop} \frac{d(T_1 d_1)}{dt} - \int_{t.start}^{t.stop} \frac{d(T_3 d_3)}{dt} \right) \right| > T_{alarm}$

OR

When $\left( \int_{t.start}^{t.stop} \frac{d(T_2 d_2)}{dt} > \int_{t.start}^{t.stop} \frac{d(T_3 d_3)}{dt} \text{ or } \int_{t.start}^{t.stop} \frac{d(T_2 d_2)}{dt} < \right.$ $\left. \int_{t.start}^{t.stop} \frac{d(T_3 d_3)}{dt} \right)$ and $\left| \left( \int_{t.start}^{t.stop} \frac{d(T_2 d_2)}{dt} - \int_{t.start}^{t.stop} \frac{d(T_3 d_3)}{dt} \right) \right| > T_{alarm}$ In Eqs. 1-4, the following definitions apply:

$T_{alarm}$ is $T_{nom} \times 1\%$ $T_{nom}$ is normal body temperature computed within 24 hours and can be defined as $T_{standard} \pm \delta T$, where $\pm \delta T$ is unique to each individual and is computed over a larger period ($\geq 24$ hours) trend analysis.

$T_{standard}$ is standard human body temperature as defined by a medical dictionary.

Measurements $T_1$, $T_2$ and $T_3$ made with the temperature sensors provide values for body temperature $T_{body}$ that can be used to determine a body temperature trend bandwidth $T_{body} \pm \delta T$.

At 208, the client device determines trend information using the temperature measurements if the physiological measurements are determined at 207 to deviate from $T_{nom}$ by more than 1%. In the event that the wearable vascular access monitor 300 transitions to a caution state, the temperature sensors 304-1, 304-2, and 304-3 will change their sampling rates of temperature measurements $T_1$, $T_2$ and $T_3$ from a slower sampling rate to a faster sampling rate. For example, the sampling rate can change from one temperature measurement per minute to one temperature measurement per second. This faster sampling rate is maintained for a predefined period, e.g., maintained for 5 to 30 minutes. The temperature measurements obtained during this predefined period are used to determine a temperature trend $T_{trend}$.

In an embodiment, when using average temperatures, a faster sampling rate also shortens the averaging time. For example, if sampling at one temperature measurement per second, then average temperatures can be obtained for every 30 seconds, thus the temperature trend $T_{trend}$ is determined with average temperature values obtained every 30 seconds for a 5 to 30 minute period. The temperature trend $T_{trend}$ is a relationship describing change in the different temperature values obtained every 30 seconds.

At 210, the client device analyzes $T_{trend}$ to determine whether to alert an emergency device. In an example, when $T_{trend}$ indicates steady temperature levels and body temperature is greater than $T_{nom}+T_{nom}\times 1\%$, then the client device sends a message to the emergency device, e.g., sends a message to a clinic treating the patient. When $T_{trend}$ indicates rising temperatures during the predefined period (e.g., 5 minutes or 30 minutes) and body temperature is greater than $T_{nom}+T_{nom}\times 1\%$, then the client device sends a message to the emergency device. When $T_{trend}$ indicates falling temperatures and body temperature is less than $T_{nom}-T_{nom}\times 1\%$, then the client device sends a message to the emergency device.

The example below is used to illustrate with numbers aspects of the process 200 as described above with respect to FIG. 3. The distances $d_1$, $d_2$, and $d_3$ are constants from the view of the placements of temperature sensors 304-1, 304-2, and 304-3. Algorithms applied to temperature readings from the temperature sensors 304 therefore account for variables of T (temperature) and t (time).

$t=t_{start}$ is an arbitrary starting value (in time) where temperature T is sampled, and $t=t_{stop}$ is a time where sampling of temperature T is finished. Each temperature sensor 304 continuously reads from $t_{start}$ to $t_{stop}$, and the resulting temperature reading is the integration of T from $t_{start}$ to $t_{stop}$.

In an embodiment, for saving power, the difference between $t_{start}$ and $t_{stop}$ is small or configurable. For example, the duration $t_{start}-t_{stop}$ can be 1 millisecond. A period of no measurements can then ensue. Afterward, the temperature sensors 304 repeat sampling temperature T for another time duration, e.g., $t_{start2}-t_{stop2}=1$ ms.

In an embodiment, two temperature readings are taken between $t_{start}$ and $t_{stop}$. For example, when the duration is a 1 ms duration, a temperature measurement T1 is made at $t_{start}$ and a temperature measurement T1.1 is made at $t_{stop}$. From T1 and T1.1, different cases can be used to determine whether the patient has an infection or elevated body temperature. Two cases are described with the T1 and T1.1 measurements:

$$T1-T1.1=0 \qquad \text{Case 1:}$$

This implies that T1 is equal to T1.1, thus there is no change in temperature during the 1 ms duration. Either T1 or T1.1 is compared against normal human body temperature (baselined as the normal body temperature of the patient). If either T1 or T1.1 is over 1% higher than the normal body temperature, then the patient can be deemed to have a fever.

$$T1>T1.1 \text{ or } T1<T1.1 \qquad \text{Case 2:}$$

This implies that there is a temperature gradient or a local heat source which signals a possibility of an infection or some kind of an anomaly. Depending on the sensor being used, the distance $d_x$ can be used to interpret location of the heat source. For example, when temperature sensor 304-1 is placed closer to the blood access point, then elevated temperatures measured at 304-1 indicate that the infection is close to temperature sensor 304-1. When there is an infection, the human body reacts and elevates body temperature near the location of the infection. Since in FIG. 3 there are three temperature sensors 304 at different distances from the blood access point 302, an algorithm can be used to combine temperature readings from the different temperature sensors 304 to obtain a more deterministic answer (independent of the ambient temperature, and the reading uncertainty from a single temperature sensor).

The previous example showed use of two measurement points in a 1 ms duration. In some embodiments, $t_{start}-t_{stop}$ is long enough to obtain more than two temperature measurements, so each temperature measured can be stored in memory and used for further analysis. The integral functions will begin to look like a simplified form of the Stokes equation and the Fundamental theorem of Calculus.

In another exemplary implementation of FIG. 2 using the exemplary configuration of sensors depicted in FIG. 3, temperature readings from the sensors 304-1, 304-2 and 304-3 are sampled to provide data points, T1, T2, and T3, respectively. Sampling frequency may be dependent on power consumption and battery life. The following discussion uses temperature sensor 304-1 as an example, but similar measurements and analyses may be performed in tandem at temperature sensors 304-2 and 304-3.

At 202, temperature sensor 304-1 samples a first reading of T1. The first reading can be a single read, i.e., a single sample, or can be a multiple read, e.g., an average of three fast samples for eliminating body/ambient noise. A multiple read and a single read both provide a single value for the first reading.

At 206, the first reading is then compared to a nominal body temperature.

At 207, if the first reading is greater than the nominal body temperature, then at 208, T1 is sampled for a longer time to determine a temperature trend. Using the temperature trend, then fever (abnormal temperature) can be determined using a rising, falling, or steady state trend of the temperature trend.

That is, after comparison of the first reading with the nominal body temperature, then the sampling time is increased to obtain more temperature readings so that the temperature trend can be determined. The temperature trend will give a direction of change as well as a rate of change so as to know whether the temperature is increasing, decreasing, or remaining steady during the longer sampling time. The longer sampling time or duration is identified above as the duration $t_{start}-t_{stop}$. The duration can be short to obtain a single T value or long to obtain multiple T values.

At 210, based on the trend information, an emergency device can be alerted.

Figure 4:
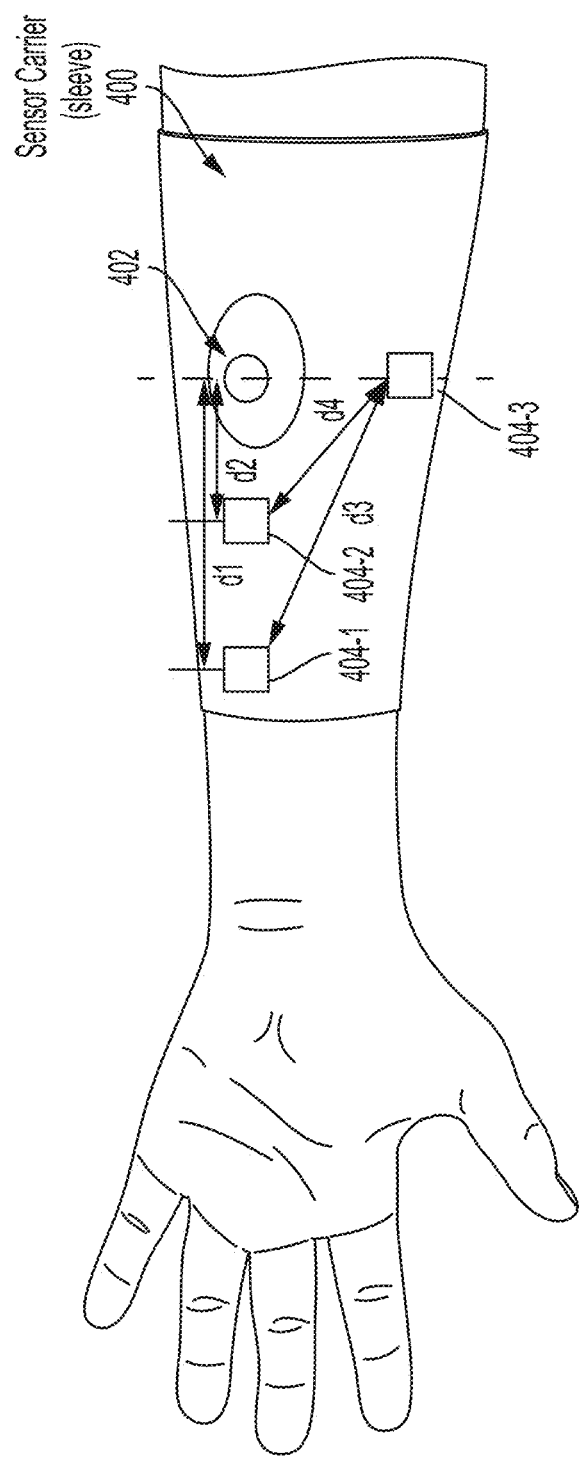
FIG. 4 illustrates a wearable vascular access monitor for gradient temperature measurements according to some embodiments of the disclosure.

FIG. 4 illustrates a wearable vascular access monitor 400 for gradient temperature measurements according to some embodiments of the disclosure. The wearable vascular access monitor 400 includes three temperature sensors 404-1, 404-2, and 404-3 placed at different locations from an access point 402. In an embodiment, the temperature sensors 404-1 and 404-2 are placed at different distances but in a same direction from the access point 402. The access point 402 is located on one side of the arm, and the temperature sensor 404-3 is located on the opposite side of the arm. For example, anterior compartment placement vs. posterior compartment placement on the forearm. In FIG. 3, the placement of the temperature sensors 304-1 and 304-2 provided differential temperature measurements which can be used to determine whether the access point 302 is infected. In FIG. 4, the placement of the temperature sensors 404-1 and 404-2, not only can indicate whether there is an infection but can also help determine a location of the infection.

The spatial distance from the access point 402 to the temperature sensor 404-1 is $d_1$. The spatial distance from the access point 402 to the temperature sensor 404-2 is $d_2$. The spatial distance from the temperature sensor 404-1 to the temperature sensor 404-3 is $d_3$, and the spatial distance from the temperature sensor 404-2 to the temperature sensor 404-3 is $d_4$.

In an embodiment, the temperature sensors 404-1, 404-2, and 404-3 sample body temperature, in degrees Celsius, at their respective locations once every minute. The wearable vascular access monitor 400 collects sensor data every minute and packages and sends the sensor data after a prescribed amount of time to a client device (not shown) at step 202.

At 204, differential temperature readings can be determined using the temperature measurements and the spatial distances in a similar manner as described above with respect to FIG. 3. Differential temperature readings between temperature sensors 404-1 and 404-2 follow Eq. 1 and differential temperature readings between temperature sensors 404-1 and 404-3 follow Eq. 2. Similarly, differential temperature readings between temperature sensors 404-2 and 404-3 are determined by Eq. 5 since distance between the temperature sensors 404-1 and 404-3 and the distance between the temperature sensors 404-2 and 404-3 are no longer equal.

$$\int_{t.start}^{t.stop} \frac{d(T_2 d_2)}{dt} - \int_{t.start}^{t.stop} \frac{d(T_3 d_4)}{dt} \qquad \text{Eq. 5}$$

At 206, to remain in the equilibrium state, as previously discussed with respect to FIG. 3, temperature measurements $T_1$, $T_2$ and $T_3$ should be within 1% of the nominal temperature $T_{nom}$. When $T_1$, $T_2$ and $T_3$ are within 1% of $T_{nom}$, the wearable vascular access monitor 300 maintains the equilibrium state. When any of $T_1$, $T_2$ or $T_3$ is not within 1% of $T_{nom}$, the wearable vascular access monitor 400 transitions to a caution state. The caution state signifies that the body temperature is too high or too low. As discussed above with respect to FIG. 3, the temperature measurements $T_1$, $T_2$ and $T_3$ can be average temperature values and not instantaneous measurements.

Similar to the case in FIG. 3, the differential temperature readings can also be used to generate an alarm when Eq. 4 is true. That is, at 205, if the differential readings exceed an alarm threshold, then at 209, an alarm is generated. As the case in FIG. 3, based on the outcome of step 207, steps 208 and 210 can be performed in a similar manner where a temperature trend $T_{trend}$ is determined and an alarm is generated using $T_{trend}$ and the body's temperature relative to the normal temperature $T_{nom}$.

Although discussed separately, embodiments provided in FIG. 3 and FIG. 4 can be combined to determine both that an infection is present and also a location of the infection. That is, in various embodiments, four or five sensors can be arranged in a wearable vascular access monitor to obtain both differential and gradient temperature measurements.

Figure 5:
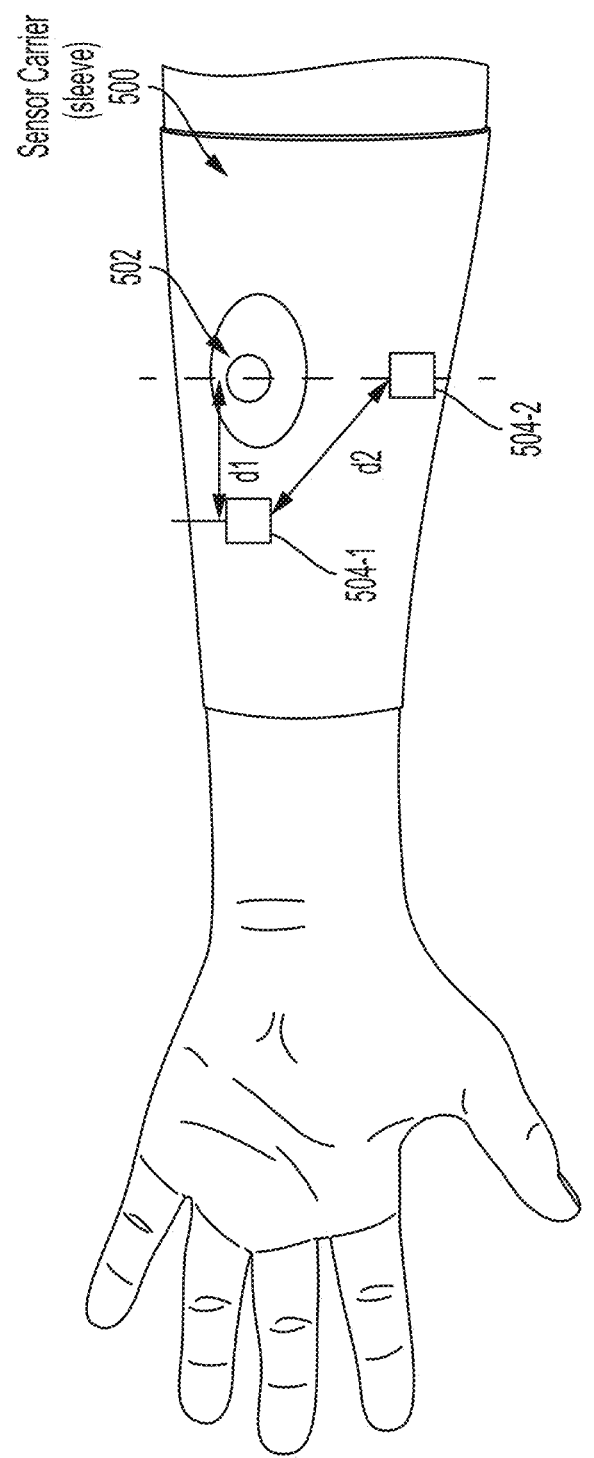
FIG. 5 illustrates a wearable vascular access monitor for pressure measurements according to some embodiments of the disclosure.

FIG. 5 illustrates a wearable vascular access monitor 500 for pressure measurements according to some embodiments of the disclosure. The wearable vascular access monitor 500 includes two pressure sensors 504-1 and 504-2 placed at different locations from an access point 502. The access point 502 is located on one side of the arm, and the pressure sensor 504-2 is located on the opposite side of the arm. The pressure sensor 504-2 is placed far from pressure sensor 504-1. Pressure measurements from the wearable vascular access monitor 500 can be used to determine whether the access point 502 is at risk of stenosis and/or hematoma. Furthermore, since pressure changes in blood vessels more rapidly than temperature, detection of access point bulging can be performed quickly.

In an embodiment, the pressure sensors 504-1 and 504-2 are placed above the patient's skin and measures pulsing below the skin. The pulsing can be used to estimate blood vessel pressure once every minute in, e.g., mmHg. The spatial distance from the access point 502 to the pressure sensor 504-1 is $d_1$. The spatial distance from the pressure sensor 504-1 to the pressure sensor 504-2 is $d_2$. The spatial distance $d_2$ should be much greater than $d_1$. The wearable vascular access monitor 500 can collect sensor data every minute and package and send the sensor data after a prescribed amount of time to a client device (not shown) at step 202.

At step 204, the differential pressure reading between the pressure sensor 504-1 and the pressure sensor 504-2 is determined via Eq. 6, where $P_1$ and $P_2$ are pressure measurements obtained from pressure sensors 504-1 and 504-2, respectively. In some embodiments, as similarly discussed above with respect to temperature values $T_1$ and $T_2$ in FIG. 3, average values of $P_1$ and $P_2$ are used in Eq. 6 instead of instantaneous values.

$$\int_{t.start}^{t.stop} \frac{d(P_1 d_1)}{dt} - \int_{t.start}^{t.stop} \frac{d(P_2 d_2)}{dt} \qquad \text{Eq. 6}$$

The differential pressure reading determined via Eq. 6 can produce different values under a normal state, when a patient is not undergoing dialysis, and under a dialysis state, when the patient is undergoing dialysis. As such, Eq. 6 can be used to obtain differential pressure readings under both the normal state and the dialysis state, and the difference in differential pressure readings between the normal state and the dialysis state can be used to determine whether physiological measurements are approximately within a normal range at step 206.

In a normal state, $P_1 = P_2 = P_{nom}$, so at 206, the client device determines whether the pressure measurements $P_1$ and $P_2$ approximate a nominal pressure $P_{nom}$. In a dialysis state, $P_1 = P_2 = P_{dialysis}$, so at 206, the client device determines whether the pressure measurements $P_1$ and $P_2$ approximate a dialysis pressure $P_{dialysis}$. Applying Eq. 6 to pressure measurements obtained in a normal state will provide diffP$_{nom}$, and applying Eq. 6 to pressure measurements obtained in the dialysis state will provide diffP$_{dialysis}$. The difference between diffP$_{nom}$ and diffP$_{dialysis}$ is diffP$_{n-d}$. In an embodiment, diffP$_{n-d}$ is bounded by a factor δP$_{n-d}$, where δP$_{n-d}$ is unique to each person and the state of the fistula or access point 502 computed over a larger period (>24 hours) trend analysis.

In an embodiment, there can be different nominal pressures for sensors 504-1 and 504-2. That is, P$_1$ values are checked to see whether they approximate P$_{nom}^1$, and P$_2$ values are checked to see whether they approximate P$_{nom}^2$. Each of P$_{nom}^1$ and P$_{nom}^2$ can have a deviation δP$_{nom}$ which sets a bounds for "approximately" as used in comparison above. δP$_{nom}$ is unique to each person an the state of the fistula or access point 502 computed over a larger period (e.g., >24 hours) trend analysis. When P$_1$ is within 1% of P$_{nom}^1$ and when P$_2$ is within 1% of P$_{nom}^2$, then the wearable vascular access monitor 500 maintains an equilibrium state. When any of these is untrue, then the wearable vascular access monitor 500 transitions to a caution state. The caution state signifies that one or more body pressure measurements is too high or too low. 1% is used as an example here, but other percentage deviations from nominal pressure can be used as limits.

At 205, the differential pressure readings of Eq. 6 can be used to determine whether to generate an alarm. In an embodiment, when Eq. 6 is nonzero and the magnitude of Eq. 6 evaluated exceeds an alarm threshold, then an alarm is generated at 209. Note that since each pressure sensor has its own nominal value, P$_{nom}^1$ or P$_{nom}^2$, there are two alarm thresholds to consider P$_{alarm}^1$ and P$_{alarm}^2$. Eq. 7 summarizes conditions for generating alarm.

$$\text{When } \left( \int_{t.start}^{t.stop} \frac{d(P_1 d_1)}{dt} > \int_{t.start}^{t.stop} \frac{d(P_2 d_2)}{dt} \text{ or } \int_{t.start}^{t.stop} \frac{d(P_1 d_1)}{dt} < \int_{t.start}^{t.stop} \frac{d(P_2 d_2)}{dt} \right) \text{ Eq. 7}$$

$$\text{and } \left| \left( \int_{t.start}^{t.stop} \frac{d(P_1 d_1)}{dt} - \int_{t.start}^{t.stop} \frac{d(P_2 d_2)}{dt} \right) \right| > P_{alarm}$$

In Eq. 7, the following definitions apply:
P$_{alarm}$ is either P$_{alarm}^1$ or P$_{alarm}^2$ depending on which sensor's measurements are being considered
P$_{alarm}^1$=P$_{nom}^1$×1%
P$_{alarm}^2$=P$_{nom}^2$×1%
P$_{nom}^1$ is normal body pressure near fistula, computed within 24 hours pressure trend analysis
P$_{nom}^2$ is normal body pressure near fistula, computed within 24 hours pressure trend analysis Measurements P$_1$ and P$_2$ made with pressure sensors provide values for pressure at specific sites and can be used to determine a body pressure trend bandwidth which is defined as P$_{1 \text{ or } 2}$±δP$_{1 \text{ or } 2}$, where ±δP$_{1 \text{ or } 2}$ is unique to each person, computed over a larger period (>24 hours).

At 208, the client device determines trend information using the pressure measurements if the physiological measurements are determined at 207 to deviate from P$_{nom}^1$ or P$_{nom}^2$ by more than 1%. In the event that the wearable vascular access monitor 500 transitions to a caution state, the pressure sensors 504-1 and 504-2 will change their sampling rates for pressure measurements P$_1$ and P$_2$ from a slower sampling rate to a faster sampling rate. For example, the sampling rate can change from one pressure measurement per minute to one pressure measurement per second. The faster sampling rate is maintained for a predefined period of time, e.g., maintained for 5 minutes. The pressure measurements obtained during this predefined period of time are used to determine pressure trends P$_{trend}^1$ and P$_{trend}^2$.

At 210, the client device analyzes each of P$_{trend}^1$ and P$_{trend}^2$ to determine whether to alert an emergency device. Each of P$_{trend}^1$ and P$_{trend}^2$ will be referred to as P$_{trend}$ and each of P$_{nom}^1$ and P$_{nom}^2$ will be referred to as P$_{nom}$ for the following description. It is understood that the superscripts can be added to obtain trend analysis for each pressure sensor's measurement. When P$_{trend}$ indicates steady pressure levels and body pressure is greater than P$_{nom}$+P$_{nom}$×1%, then the client device sends a message to the emergency device, e.g., sends a message to a clinic treating the patient. When P$_{trend}$ indicates rising pressure levels during the predefined period of time and body pressure is greater than P$_{nom}$+P$_{nom}$×1%, then the client device sends a message to the emergency device. When P$_{trend}$ indicates falling pressure levels and body pressure is less than P$_{nom}$−P$_{nom}$×1%, then the client device sends a message to the emergency device.

Although two pressure sensors are provided in FIG. 5, more than two pressure sensors can be included in the wearable vascular access monitor 500. Placement of sensors can be a combination of that shown for temperature sensors in FIGS. 3-4. Multitude sensors being used provides advantages previously described in the temperature sensor setting, e.g., decision based voting, high-reliable system decisions based on triple-redundant sensor data, and so on.

Furthermore, although FIGS. 3 and 4 did not describe a dialysis state with respect to temperature, in some embodiments, temperature measurements during dialysis are also tracked. That is, temperature readings from the temperature sensors can be compared against a T$_{dialysis}$ to determine whether to exit an equilibrium state. Furthermore, a diffT$_{nom}$ and a diffT$_{dialysis}$ can be obtained for each of Eqs. 1-3 during a normal state and during a dialysis state, respectively. Furthermore, a diffT$_{n-d}$ can be defined as diffT$_{nom}$−diffT$_{dialysis}$. Since the use of measurement metrics in the normal state and the dialysis state is already described above with respect to pressure, similar descriptions are omitted with respect to temperature.

Figure 6:
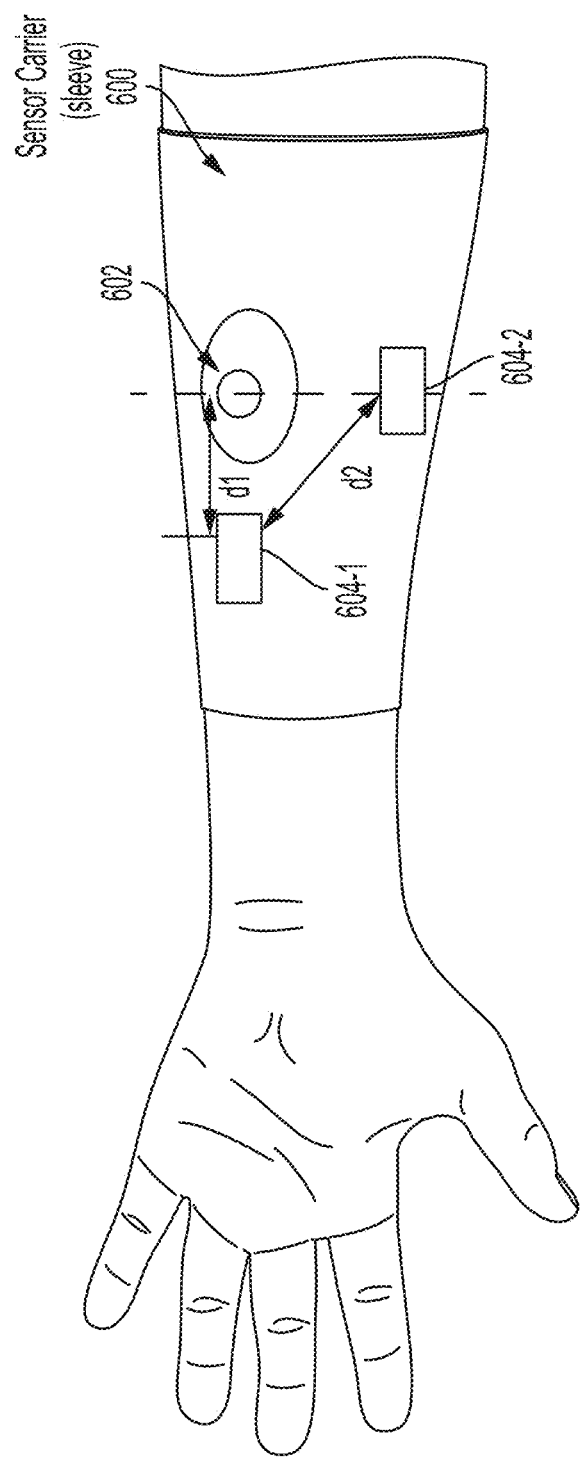
FIG. 6 illustrates a wearable vascular access monitor for SpO2 measurements according to some embodiments of the disclosure.

FIG. 6 illustrates a wearable vascular access monitor 600 for SpO2 (blood oxygen saturation) measurements according to some embodiments of the disclosure. The wearable vascular access monitor 600 includes two blood oxygen saturation or SpO2 sensors 604-1 and 604-2 placed at different locations from an access point 602. The access point 602 is located on one side of the arm, and the SpO2 sensor 504-2 is located on the opposite side of the arm. The SpO2 sensor 504-2 is placed far from the SpO2 sensor 504-1. SpO2 measurements from the wearable vascular access monitor 600 can be used to check for onset of anemia around the area of the access point 602. SpO2 measurements can also provide information on level of iron deficiency there is in the body.

The spatial distance from the access point 602 to the SpO2 sensor 604-1 is d$_1$. The spatial distance from the SpO2 sensor 604-1 to the pressure sensor 604-2 is d$_2$. The spatial distance d$_2$ should be much greater than d$_1$. The wearable vascular access monitor 600 can collect sensor data every minute and package and send the sensor data after a prescribed amount of time to a client device (not shown) at step 202.

At step 204, the differential SpO2 reading between the SpO2 sensor 604-1 and the SpO2 sensor 604-2 is determined via Eq. 8, where SPO2$_1$ and SPO2$_2$ are SpO2 measurements obtained from SpO2 sensors 604-1 and 604-2, respectively.

$$\int_{t.start}^{t.stop} \frac{d(SPO2_1 d_1)}{dt} - \int_{t.start}^{t.stop} \frac{d(SPO2_2 d_2)}{dt} \quad \text{Eq. 8}$$

The differential SpO2 reading determined via Eq. 8 can produce different values under a normal state, when a patient is not undergoing dialysis, and under a dialysis state, when the patient is undergoing dialysis. As such, Eq. 8 can be used to obtain differential SpO2 readings under both the normal state and the dialysis state, and the difference in differential SpO2 readings between the normal state and the dialysis state can be used to determine whether physiological measurements are approximately within a normal range at step 206.

In a normal state, $SPO2_1 = SPO2_2 = SPO2_{nom}$, so at 206, the client device determines whether the SpO2 measurements $SPO2_1$ and $SPO2_2$ approximate a nominal blood oxygen saturation $SPO2_{nom}$. In a dialysis state, $SPO2_1 = SPO2_2 = SPO2_{dialysis}$, so at 206, the client device determines whether the SpO2 measurements $SPO2_1$ and $SPO2_2$ approximate a dialysis blood oxygen saturation $SPO2_{dialysis}$. Applying Eq. 8 to SpO2 measurements obtained in a normal state will provide $diffSPO2_{nom}$, and applying Eq. 8 to SpO2 measurements obtained in the dialysis state will provide $diffSPO2_{dialysis}$. The difference between $diffSPO2_{nom}$ and $diffSPO2_{dialysis}$ is $diffSPO2_{n-d}$. In an embodiment, $diffSPO2_{n-d}$ is bounded by a factor $\delta SPO2_{n-d}$, where $\delta SPO2_{n-d}$ is unique to each person and the state of the fistula or access point 602 computed over a larger period (>24 hours) trend analysis.

In an embodiment, there can be different nominal SpO2 values for SpO2 sensors 604-1 and 604-2. That is, $SPO2_1$ values are checked to see whether they approximate $SPO2_{nom}^1$ and $SPO2_2$ values are checked to see whether they approximate $SPO2_{nom}^2$. Each of $SPO2_{nom}^1$ and $SPO2_{nom}^2$ can have a deviation of $\delta SPO2_{nom}$ which sets a bounds for "approximately" as used in comparison above. $\delta SPO2_{nom}$ is unique to each person and the state of the fistula or access point 602 computer over a larger period (e.g., >24 hours) trend analysis. When $SPO2_1$ is within 1% of $SPO2_{nom}^1$ and when $SPO2_2$ is within 1% of $SPO2_{nom}^2$, then the wearable vascular access monitor 600 maintains an equilibrium state. When any of these is untrue, then the wearable vascular access monitor 600 transitions to a caution state. The caution state signifies that one or more body SpO2 measurements is too high or too low. 1% is used as an example here, but other percentage deviations, e.g., 2%, from nominal pressure can be used as limits.

At 205, the differential SpO2 readings of Eq. 8 can be used to determine whether to generate an alarm. In an embodiment, when Eq. 8 is nonzero and the magnitude of Eq. 8 evaluated exceeds an alarm threshold, then an alarm is generated. Note that since each SpO2 sensor has its own nominal value, $SPO2_{nom}^1$ or $SPO2_{nom}^2$, there are two alarm thresholds to consider $SPO2_{alarm}^1$ and $SPO2_{alarm}^2$. Eq. 9 summarizes conditions for generating an alarm.

$$\text{When } \left( \int_{t.start}^{t.stop} \frac{d(SPO2_1 d_1)}{dt} > \int_{t.start}^{t.stop} \frac{d(SPO2_2 d_2)}{dt} \text{ or } \int_{t.start}^{t.stop} \frac{d(SPO2_1 d_1)}{dt} < \int_{t.start}^{t.stop} \frac{d(SPO2_2 d_2)}{dt} \right. \quad \text{Eq. 9}$$

-continued
$$\left. \left( \int_{t.start}^{t.stop} \frac{d(SPO2_1 d_1)}{dt} - \int_{t.start}^{t.stop} \frac{d(SPO2_2 d_2)}{dt} \right) \right| > SPO2_{alarm}$$

In Eq. 9, the following definitions apply:
$SPO2_{alarm}$ is either $SPO2_{alarm}^1$ or $SPO2_{alarm}^2$ depending on which sensor's measurements are being considered
$SPO2_{alarm}^1 = SPO2_{nom}^1 \times 1\%$
$SPO2_{alarm}^2 = SPO2_{nom}^2 \times 1\%$
$SPO2_{nom}^1$ is normal body SpO2 level near fistula, computed within 24 hours SpO2 trend analysis
$SPO2_{nom}^2$ is normal body SpO2 level near fistula, computed within 24 hours SpO2 trend analysis Measurements $SPO2_1$ and $SPO2_2$ made with SpO2 sensors provide values for blood oxygen saturation levels at specific sites and can be used to determine a body SpO2 trend bandwidth which is defined as $SPO2_{1 \text{ or } 2} \pm \delta SPO2_{1 \text{ or } 2}$, where $\pm \delta SPO2_{1 \text{ or } 2}$ is unique to each person, computed over a larger period (>24 hours).

At 208, the client device determines trend information using the SpO2 measurements if the physiological measurements are determined at 207 to deviate from $SPO2_{nom}^1$ and $SPO2_{nom}^2$ by more than 1%. In the event that the wearable vascular access monitor 600 transitions to a caution state, the SpO2 sensors 604-1 and 604-2 will change their sampling rates for SpO2 measurements $SPO2_1$ and $SPO2_2$ from a slower sampling rate to a faster sampling rate. For example, the sampling rate can change from one SpO2 measurement per minute to one SpO2 measurement per second. The faster sampling rate is maintained for a predefined period of time, e.g., maintained for 5 to 30 minutes. The SpO2 measurements obtained during this predefined period of time are used to determine blood oxygen saturation trends $SPO2_{trend}^1$ and $SPO2_{trend}^2$.

At 210, the client device analyzes each of $SPO2_{trend}^1$ and $SPO2_{trend}^2$ to determine whether to alert an emergency device. Each of $SPO2_{trend}^1$ and $SPO2_{trend}^2$ will be referred to as $SPO2_{trend}$ and each of $SPO2_{nom}^1$ and $SPO2_{nom}^2$ will be referred to as $SPO2_{nom}$ for the following description. It is understood that the superscripts can be added to obtain trend analysis for each pressure sensor's measurement. When $SPO2_{trend}$ indicates steady SpO2 levels and body SpO2 is greater than $SPO2_{nom} + SPO2_{nom} \times 1\%$, then the client device sends a message to the emergency device, e.g., sends a message to a clinic treating the patient. When $SPO2_{trend}$ indicates rising SpO2 levels during the predefined period of time and body SpO2 is greater than $SPO2_{nom} + SPO2_{nom} \times 1\%$, then the client device sends a message to the emergency device. When $SPO2_{trend}$ indicates falling SpO2 levels and body SpO2 is less than $SPO2_{nom} - SPO2_{nom} \times 1\%$, then the client device sends a message to the emergency device.

Although described separately, each of the embodiments of FIGS. 3-6 is combinable. That is, different types of sensors can be provided in a wearable vascular access monitor to provide information on infection and hematoma using temperature and pressure. Furthermore, other types of sensors like accelerometers and force sensors can be used to determine whether the patient is putting too much weight or is moving his arm too quickly. Information obtained by these sensors can be used to alert emergency contacts so that they can inform the patient on how to better be aware of his posture so as to not generate such alerts. Embodiments of the disclosure provide a way of educating patients on proper maintenance of fistulas to combat any lack of awareness of potentially dangerous behavior or improper maintenance on the patients' part.

Embodiments of the disclosure can be used to monitor peritoneal dialysis access points or to monitor other surgical grafts. A wearable vascular access monitor according to embodiments of the disclosure can be provided as a band especially when all sensors are placed on a same side. For example, in FIG. 4, a band containing sensors 404-1, 404-2, and 404-3 can be worn close to the access point 402.

In an example, a patient slips on a wearable vascular access monitor according to embodiments of the disclosure. The wearable vascular access monitor is fitted with sensor straps that prevent the sensors from moving once in place. The system then turns on automatically after the sensor straps are fixed. The sensors provide pressure and temperature data which are later transmitted to a client device for storage. After every half hour, the transmitted data is assessed to determine whether the access point being monitored is okay. A physician/clinic is alerted by the client device if there is an anomaly. In an embodiment, the wearable vascular access monitor is worn during dialysis to inform a physician on how to adjust blood flow rate based on performance of the access point.

Figure 7:
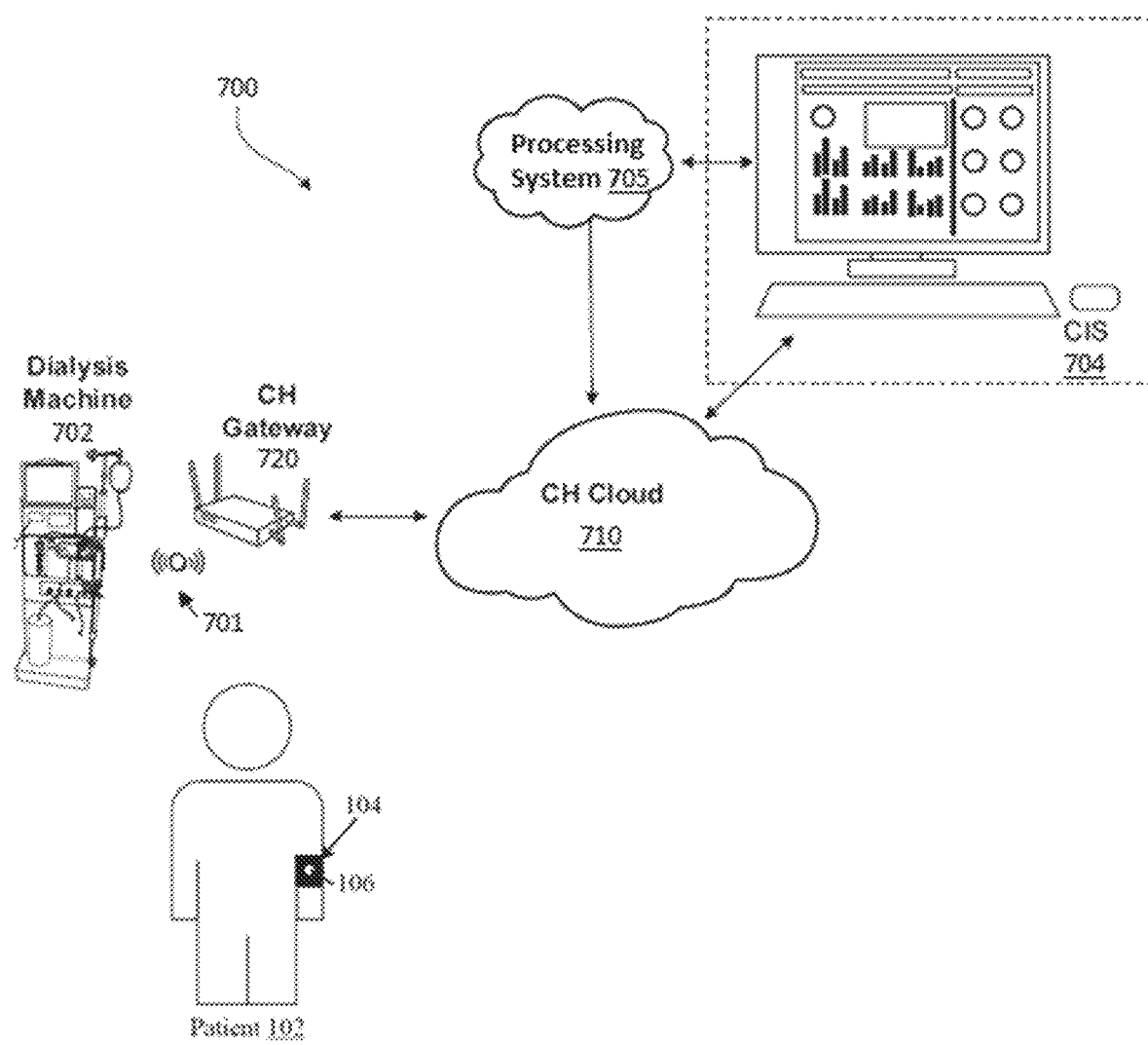
FIG. 7 is a schematic illustration showing an example of a connected health (CH) system that may include, among other things, a processing system, a CH cloud service and a CH gateway that may be used in connection with vascular access monitoring systems according to some embodiments of the disclosure.

FIG. 7 is a schematic illustration showing an example of a connected health (CH) system 700 that may include, among other things, a processing system 705, a CH cloud 710 and a gateway (CH Gateway) 720 that may be used in connection with network aspects of the system described herein. The processing system 705 may be a server and/or cloud-based system that processes, compatibility checks and/or formats medical information, including prescription information generated at a clinical information system (CIS) 704 of a clinic or hospital, in connection with data transmission operations of the CH system 700. The CH system 700 may include appropriate encryption and data security mechanisms. The CH cloud 710 may be a cloud-based application or system that serves as a communication pipeline (e.g., facilitates the transfer of data) among components of the CH system 700 via connections to a network, the Internet.

The gateway 720 may serve as a communication device facilitating communication among components of the CH system 700 and, for example, may function as a client device like the client devices 108 discussed elsewhere herein. In various embodiments, the gateway 720 is in communication with a dialysis machine 702, such as a home hemodialysis machine, via a wireless connection 701, such as a Bluetooth, Wi-Fi and/or other appropriate type of local or short-range wireless connection. The gateway 720 may also be in connection with the CH cloud service 710 via a secure network (e.g. Internet) connection. The gateway 720 is configured to transmit/receive data to/from the CH cloud 710 and transmit/receive data to/from the dialysis machine 702. The gateway 720 may also facilitate communication between peripheral devices, such as the wearable vascular access monitor 104 worn at the access point 106 by the patient 102.

In an embodiment, during dialysis, the dialysis machine 702 interfaces with the patient 102 at the dialysis access point 106 (e.g., AVF). The dialysis machine 702 extracts blood from the patient via a blood extraction needle, filters the blood, and reintroduces the blood to the patient via a blood injection needle. That is, during dialysis, the dialysis machine 702 pumps blood out of the patient via the blood extraction needle, and using tubing, provides the blood to a dialyzer where the blood is filtered. The dialysis machine 702 then circulates the blood via tubing to the blood injection needle for reintroduction to the patient.

As the patient 102 is undergoing dialysis, the wearable vascular access monitor 104 measures conditions proximate to the access point 106 and generates sensor data, as already described herein in previous embodiments. The wearable vascular access monitor 104 provides sensor data to the gateway 720. The dialysis machine 702, connected to the gateway 720 via the wireless connection 701, provides treatment information to the gateway 720. Treatment information can include blood pump rate, dialysate pump rate, type of dialysate used, treatment start time, treatment time elapsed, measured hematocrit, and so on. The dialysis machine 702 may include a blood sensor, for example as described in U.S. Patent Publication No. 2016/0377530, which is hereby incorporated by reference herein in its entirety.

The gateway 720 can analyze the sensor data from the wearable vascular access monitor 104 in context of the treatment information from the dialysis machine 702 and can provide the treatment information and the sensor data to the CH cloud 710 for further processing and analysis. The gateway 720 can determine that the patient 102 is undergoing dialysis via the treatment information received. That way, the gateway 720 can classify sensor data as either nominal or under dialysis. The gateway 720 can also receive patient electronic records from the CH cloud 710 to inform its analysis.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A system for monitoring a vascular access comprising: a wearable vascular access monitor comprising:
   a plurality of sensors placed at different locations and configured to provide a plurality of physiological measurements, wherein the plurality of sensors comprise a first sensor and a second sensor, wherein the first sensor is located at a first distance away from a point of the vascular access and configured to provide a first physiological measurement of the plurality of physiological measurements, and wherein the second sensor is located at a second distance away from the vascular access point and configured to provide a second physiological measurement of the plurality of physiological measurements; and
   a communication interface configured to facilitate communications with a client device; and
   the client device, wherein the client device is configured to:
      determine a first differential reading using the first physiological measurement, the first distance, the second physiological measurement, and the second distance, wherein the first distance is a distance between the first sensor and the vascular access point and the second distance is a distance between the second sensor and the vascular access point;
      determine whether the first differential reading exceeds a first threshold; and
      send an alert to an emergency device in response to the first differential reading exceeding the first threshold.

2. The system according to claim 1, wherein the plurality of sensors comprise temperature sensors, pressure sensors, and/or blood oxygen saturation sensors.

3. The system according to claim 1, wherein the client device is further configured to:
   determine whether the first physiological measurement or the second physiological measurement deviates from a nominal value by a second threshold.

4. The system according to claim 3, wherein the client device is further configured to:
   determine trend information for the plurality of physiological measurements in response to the first physiological measurement or the second physiological measurement deviating from the nominal value by the second threshold, the trend information indicating whether the plurality of physiological measurements are steady, falling, or rising; and
   determine whether to alert the emergency device based on the trend information.

5. The system according to claim 3, wherein the client device is further configured to:
   send an alert to the emergency device in response to the first physiological measurement or the second physiological measurement deviating from the nominal value by the second threshold.

6. The system according to claim 3, wherein the client device is further configured to:
   in response to the first physiological measurement or the second physiological measurement deviating from the nominal value by the second threshold, cause the plurality of sensors to provide the plurality of physiological measurements at a caution sample rate, wherein the caution sample rate is higher than an equilibrium sample rate that is used when the plurality of physiological measurements do not deviate from the nominal value by the second threshold.

7. The system according to claim 1, wherein determining the first differential reading is in response to a change in the first physiological measurement or the second physiological measurement.

8. The system according to claim 1, wherein the first sensor is a first temperature sensor and the second sensor is a second temperature sensor, and the vascular access point is located between the first temperature sensor and the second temperature sensor.

9. The system according to claim 8, wherein the alert sent to the emergency device indicates detection of an infection.

10. The system according to claim 1, wherein the first sensor is a first temperature sensor and the second sensor is a second temperature sensor, and the second temperature sensor is located between the first temperature sensor and the vascular access point.

11. The system according to claim 10, wherein the client device is further configured to determine gradient temperature measurements proximate to the vascular access point based on the first physiological measurement and the second physiological measurement, and wherein the alert sent to the emergency device is further based on the gradient temperature measurements and indicates a location of an infection.

12. The system according to claim 1, wherein the first sensor is a first pressure sensor and the second sensor is a second pressure sensor, wherein the first and the second physiological measurements are first and second pressure measurements, and wherein the alert sent to the emergency device is further based on the first and the second pressure measurements and indicates detection of a hematoma or stenosis.

13. The system according to claim 1, wherein the first sensor is a first blood oxygen saturation sensor and the second sensor is a second blood oxygen saturation sensor, wherein the first and second physiological measurements are first and second oxygen saturation measurements, and wherein the alert sent to the emergency device is further based on the first and the second oxygen saturation measurements and indicates detection iron deficiency around the vascular access.

14. The system according to claim 1, wherein the plurality of sensors further comprise a third sensor configured to provide a third physiological measurement of the plurality of physiological measurements, wherein the first, second, and third sensors are located at a equidistant third distance away from each other, and
   wherein the client device is further configured to:
      determine a second differential reading using the first physiological measurement, the first distance, the third physiological measurement, and the equidistant third distance; and
      determine a third differential reading using the second physiological measurement, the second distance, the third physiological measurement, and the equidistant third distance; and
   wherein sending the alert to the emergency device is further based on the second differential reading and the third differential reading.

15. The system according to claim 1, wherein the plurality of sensors further comprise a third sensor configured to provide a third physiological measurement of the plurality of physiological measurements, wherein the first sensor and the third sensor are located at a third distance away from each other, wherein the second sensor and the third sensor are located at a fourth distance away from each other, wherein the third distance is different from the fourth distance, and
wherein the client device is further configured to:
determine a second differential reading using the first physiological measurement, the first distance, the third physiological measurement, and the third distance; and
determine a third differential reading using the second physiological measurement, the second distance, the third physiological measurement, and the fourth distance; and
wherein sending the alert to the emergency device is further based on the second differential reading and the third differential reading.

16. The system according to claim 15, wherein the client device is further configured to determine a location of an infection based on the third differential reading.

17. One or more non-transitory computer-readable media having processor-executable instructions stored thereon for monitoring a vascular access, wherein the processor-executable instructions, when executed, facilitate:
receiving, from a plurality of sensors of a wearable access monitor placed at different locations, a plurality of physiological measurements, wherein the plurality of physiological measurements comprise a first physiological measurement and a second physiological measurement, wherein the first physiological measurement is from a first sensor of the plurality of sensors and the first sensor is located at a first distance away from a point of the vascular access, and wherein the second physiological measurement is from a second sensor of the plurality of sensors and the second sensor is located a second distance away from the vascular access point;
determining a first differential reading using the first physiological measurement, the second physiological measurement, the first distance, and the second distance, wherein the first distance is a distance between the first sensor and the vascular access point and the second distance is a distance between the second sensor and the vascular access point;
determining whether the first differential reading exceeds a first threshold; and
sending an alert to an emergency device in response to the first differential reading exceeding the first threshold.

18. The one or more non-transitory computer-readable media according to claim 17, wherein the plurality of sensors comprise temperature sensors, pressure sensors, and/or blood oxygen saturation sensors.

19. The one or more non-transitory computer-readable media according to claim 17, wherein the processor-executable instructions, when executed, further facilitate:
determining whether the first physiological measurement or the second physiological measurement deviates from a nominal value by a second threshold.

20. The one or more non-transitory computer-readable media according to claim 19, wherein the processor-executable instructions, when executed, further facilitate:
determining trend information for the plurality of physiological measurements in response to the first physiological measurement or the second physiological measurement deviating from the nominal value by the second threshold, the trend information indicating whether the plurality of physiological measurements are steady, falling, or rising; and
determining whether to alert the emergency device based on the trend information.

21. The one or more non-transitory computer-readable media according to claim 19, wherein the processor-executable instructions, when executed, further facilitate:
sending an alert to the emergency device in response to the first physiological measurement or the second physiological measurement deviating from the nominal value by the second threshold.

22. A device for monitoring a vascular access, the device comprising a processor and a non-transitory computer-readable medium having processor-executable instructions stored thereon, wherein the processor-executable instructions, when executed by the processor, facilitate performance of the following:
receiving, from a plurality of sensors of a wearable access monitor placed at different locations, a plurality of physiological measurements, wherein the plurality of physiological measurements comprise a first physiological measurement and a second physiological measurement, wherein the first physiological measurement is from a first sensor of the plurality of sensors and the first sensor is located at a first distance away from a point of the vascular access, and wherein the second physiological measurement is from a second sensor of the plurality of sensors and the second sensor is located a second distance away from the vascular access point;
determining a first differential reading using the first physiological measurement, the second physiological measurement, the first distance, and the second distance, wherein the first distance is a distance between the first sensor and the vascular access point and the second distance is a distance between the second sensor and the vascular access point;
determining whether the first differential reading exceeds a first threshold; and
sending an alert to an emergency device in response to the first differential reading exceeding the first threshold.

23. The device according to claim 22, wherein the plurality of sensors comprise temperature sensors, pressure sensors, and/or blood oxygen saturation sensors.

24. A method for monitoring a vascular access comprising:
receiving, from a plurality of sensors of a wearable access monitor placed at different locations, a plurality of physiological measurements, wherein the plurality of physiological measurements comprise a first physiological measurement and a second physiological measurement, wherein the first physiological measurement is from a first sensor of the plurality of sensors and the first sensor is located at a first distance away from a point of the vascular access, and wherein the second physiological measurement is from a second sensor of the plurality of sensors and the second sensor is located a second distance away from the vascular access point;
determining a first differential reading using the first physiological measurement, the second physiological measurement, the first distance, and the second distance, wherein the first distance is a distance between the first sensor and the vascular access point and the second distance is a distance between the second sensor and the vascular access point;
determining whether the first differential reading exceeds a first threshold; and
sending an alert to an emergency device in response to the first differential reading exceeding the first threshold.

25. The method according to claim 24, wherein the plurality of sensors comprise temperature sensors, pressure sensors, and/or blood oxygen saturation sensors.

26. The method according to claim 24, further comprising:
   determining whether the first physiological measurement or the second physiological measurement deviates from a nominal value by a second threshold.

* * * * *